United States Patent
Künnecke et al.

(10) Patent No.: US 6,562,211 B1
(45) Date of Patent: May 13, 2003

(54) MEMBRANE PROBE FOR TAKING SAMPLES OF AN ANALYTE LOCATED IN A FLUID MEDIUM

(75) Inventors: Wolfgang Künnecke, Braunschweig (DE); Matthias Beuse, Hannover (DE); Detlef Hanisch, Wolfenbürtel (DE); Georg Penteridis, Braunschweig (DE)

(73) Assignee: Trace Biotech AG (DE)

( * ) Notice: Subject to any disclaimer, the term of this patent is extended or adjusted under 35 U.S.C. 154(b) by 0 days.

(21) Appl. No.: 09/830,196

(22) PCT Filed: Oct. 16, 1999

(86) PCT No.: PCT/DE99/03326

§ 371 (c)(1), (2), (4) Date: Jun. 28, 2001

(87) PCT Pub. No.: WO00/25107

PCT Pub. Date: May 4, 2000

(30) Foreign Application Priority Data

Oct. 22, 1998 (DE) .......................... 198 48 542

(51) Int. Cl.⁷ .............................................. G01N 27/404
(52) U.S. Cl. ........................................ 204/415; 204/279
(58) Field of Search ................................ 204/415, 279, 204/252–266

(56) References Cited

U.S. PATENT DOCUMENTS 3,445,369 A * 5/1969 Porter et al.
4,404,284 A 9/1983 Heider et al.

FOREIGN PATENT DOCUMENTS

| DE | 2 310 264 | 9/1973 | ............ G01N/1/04 |
| DE | 31 26 648 A1 | 1/1983 | ............ G01N/27/40 |
| EP | 0 043 537 A1 | 6/1982 | ............ G01N/1/22 |
| GB | 1 375 603 | 11/1974 | ............ B01D/13/00 |
| WO | WO 96/07885 | 3/1996 | ............ G01N/1/10 |
| WO | WO 97/08533 | 3/1997 | ............ G01N/71/22 |

* cited by examiner

Primary Examiner—T. Tung
(74) Attorney, Agent, or Firm—Pendorf & Cutliff

(57) ABSTRACT

The inventive prove (10) for taking samples of an analyte located in the fluid medium has a membrane which closes the probe (10) to the outside and which is permeable to the analyte, a flow-through cell which is configured behind the membrane, a probe part (14) with at least one incoming line and one outgoing line leading to or from the flow-through cell, and a membrane holder (160) which, together with the membrane, forms a replaceable unit of the probe part (14) together with the incoming line and outgoing line.

7 Claims, 6 Drawing Sheets

MEMBRANE PROBE FOR TAKING SAMPLES OF AN ANALYTE LOCATED IN A FLUID MEDIUM

BACKGROUND OF THE INVENTION

1. Field of the Invention

The invention concerns a probe for taking samples of an analyte located in the fluid medium, the probe including a membrane which closes the probe to the outside, the membrane being permeable to the analyte, a flow-through cell positioned behind the membrane, and at least one incoming and outgoing line leading to or from the flow-through cell.

2. Description of The Related Art

In chemical analysis it is frequently desired that particular components of a system are detected or monitored and that this occurs via a measurement probe. To this end various probes are in use, each designed depending upon the particularities of the various analytical possibilities. For example, probes are known which contain electrodes or polarographic sensors and which are closed off towards the outside—that is, with respect to the medium being analyzed—by a membrane. Such probes contain, among other things, a stationary fluid, such as an electrolyte or a buffer solution. Further, it is known to have probes for measurement using a flow-through process, that is, that the substance to be analyzed (the analyte), after passing through the membrane and entring into the probe, is transported to a remote measuring system for taking measurements.

In DE-AS 26 50 730 B1 and WO 97/08533 A2 a submerged dialyzer is described, in which a membrane is applied directly upon a replaceable probe part, which includes an incoming and outgoing line. The membrane is so tensioned over the head of the probe part, that it is removable. In order to guarantee an even distribution of the buffer under the membrane, ruffles or ridges are provided in the head of the probe part. Since the membrane is frequently very thin and sensitive, changing out of the membrane, and cupping of the membrane over the head, is quite difficult. Besides, the exchange surface between the fluid medium situated outside of the membrane and the medium flowing through the ridges is relatively large and unspecified.

In DE-OS 2 310 264 a similar probe is described, in which the incoming and outgoing lines are wound in the form of a helix.

In EP 0 054 537 A1 a probe carrier is described, in which the membrane is applied directly upon the probe carrier. The arrangement is so provided on a housing, that the membrane cannot be replaced in a simple manner. Besides this, the exchange surface over the flow-through cell cannot be varied.

In DE 297 01 652 U1 a probe is described, in which a membrane is laid upon the probe part and is secured from the outside using a membrane holder. The membrane holder has a defined opening, so that a fluid medium can pass through the opening to the membrane and from this to a flow-through cell. The exchange surface between the membrane and the flow-through cell is determined by a through-hole, which is situated behind the membrane in the probe part. Since the membrane is clamped between the probe part and the membrane holder, the replacement of the membrane is difficult. Besides this, the exchange surface area is permanently predetermined by the probe and cannot be varied.

A similar probe is described in DE-OS 31 26 648 A1, in which the membrane is introduced in the opening of a membrane holder which can be screwed upon the probe. Thereby the problem occurs, that the membrane surface towards outside is predetermined by the through-hole in the membrane holder, which at the same time determines the exchange surface.

In WO 96/07885 A1 a probe with a circular shaped surface is described, in which a membrane is glued directly upon a membrane holder, and wherein a communication channel for an incoming and an outgoing line is provided between the membrane and the membrane holder. The probe has the disadvantage, that the membrane is not easy to replace and is adhered. It cannot be employed in extreme environmental conditions, since an adhesive bond in this form cannot be made sterile-tight and would dissolve or release during steam sterilization. Further, the membrane is completely open upwards and offers a maximal exchange surface.

The herein described probe type is suitable for taking samples from a fluid medium, wherein the analyte comes into contact with an acceptor (medium) after entry into the probe, which via an incoming and outgoing line is channeled to a flow-through cell proved in the probe.

SUMMARY OF THE INVENTION

It is thus the task of the invention, to provide a probe, in which the membrane and the membrane holder are easy to replace and with which a defined exchange surface with the flow-through cell can easily be varied, while using an otherwise identical or standard membrane. The probe should herein be capable of being employed in extreme analyte conditions, that is, should be sterilizable by steam and should be sterile-tight.

The probe is to be so designed or equipped, that even minute amounts of analyte can be removed, and that sample volumes can be kept small, insofar as this is desired.

For solving this task provision is made to introduce the membrane between two membrane seals and with these to form a unit, wherein the membrane seals respectively have a passage or through-hole to the membrane holder or as the case may be the probe part, and the unit is provided between the membrane holder and the probe part and is securable to the probe part via the membrane holder in a replaceable yet sealing manner. The membrane holder is in the form of a gland and provides, by means of the through-holes of the membrane seals, for only a defined limited surface of the membrane to be exposed over the flow-through cell.

It is thus proposed, that the membrane holder defines the exchange surface over the flow-through cell. The membrane holder is thereby positioned before the membrane and the probe part and sealingly and releaseably clamps the membrane tightly to the probe part. The membrane is provided between two membrane seals and forms thereby a sandwich structure type unit, which is easily exchangeable and easy to manipulate and besides this has a good sealing effect. Thereby the membrane and membrane holder are removable as a single unit, so that the exchange surface can be changed by a simple unscrewing of the unit comprised of membrane and membrane holder and replaced by another unit dimensioned as needed.

An elementary difference in comparison to the conventional probes is comprised therein, that the membrane is provided tightly or fixedly between the membrane seals, so that the normally thin and sensitive membrane can be exchanged together with the membrane seals, wherein this unit and the membrane holders are premade.

The inventive probe is preferably a pure sample-taking probe; the actual measurement is undertaken in conventional manner outside of the probe, but it can however also occur within the flow-through cell. In the later case the flow-through cell must be supplementally provided with at least one sensor as well as circuits or conductors going to the sensor for control of the measurement process and for relaying or communicating the measurement results. These measures as such are known and are thus not described in greater detail herein.

The measurement can occur via various measurement processes. If the measurement is carried out outside of the probe, then there is through the conduits an acceptor flow directed to the flow-through cell which is closed off to the outside via the membrane and subsequently flows out of the probe through the outgoing lines and is supplied to the measurement unit. The acceptor flow can be directed continuously through the probe. It is possible, to interrupt the acceptor flow, so that a defined enrichment of the analyte defusing through the membrane can occur in the acceptor. The control of the acceptor flow occurs however likewise from outside the probe and is thus not discussed in greater detail herein.

An important characteristic of the invention is comprised therein, that the membrane is connected to an isolated membrane holder.

The production or premanufacture of a unit comprised of membrane and membrane holder offers many advantages. First, the unit comprised of membrane and membrane holder makes possible a simple exchange of the membrane with another membrane connected with an appropriate membrane holder. In this manner, used membranes can be easily changed and respectively different membranes can be used selectively for various measurement process and/or analytes using the same probe. Since the membrane is connected with the holder, the exchange of the frequently thin and sensitive membrane is easy to accomplish. The membrane can for example of adhered to the holder, or it can be secured to the holder via suitable securing means.

A further important feature of the invention is comprised therein, that the membrane holder forms a gland and only a defined surface of the membrane (over the flow-through cell) is exposed as an exchange surface, through which the analyte can penetrate into the flow-through cell from outside. For the measurement and evaluation of the analyte it is important, that the exchange surface between the fluid medium originally containing the analyte and the acceptor situated in the flow-through cell is precisely determinable, and that one can in certain cases exercise influence over this exchange surface.

The membrane holder is thus so designed, that a defined surface area of the membrane situated over the flow-through cell and connected therewith is exposed, through which the analyte can penetrate. It is thus possible to have available various units of membrane and membrane holde for conducting various measurements in which the membrane holder exposes respectively various surface areas with an otherwise identical membrane.

In a further development of the invention it is envisioned, that the flow-through cell within the probe has an elongate form along the membrane. The elongate form is a particularly suitable geometry for a flow-through measurement, since a discontinuous or interrupted flow process, with uniform-as-possible acceptor dwell times, can be achieved. Besides this it is useful, to maintain the acceptor below the membrane to a thin layer thickness.

The flow-through cell can—in one embodiment of the invention—be formed or designed having one channel introduced in the membrane and one in the seal which may in certain cases be associated therewith. Thereby it is optimally achieved, that the acceptor medium during the course of the exchange or, as the case may be, the entry of analyte, occurs in a thin layer directly along the membrane.

The incoming and outgoing lines can advantageously be provided on the back side of the elongated flow-through cell.

In an advantageous embodiment of the invention the incoming and outgoing lines are comprised of capillaries, between which the (preferably elongate, channel-like) flow-through cell is provided.

It is further advantageous, that the probe as a whole is shaped like a tube, wherein the flow-through cell and the unit comprised of membrane and membrane holder are provided on one end of the tube and wherein the incoming and outgoing lines lead to connections on the other end of the tube. Depending upon the selected length of this tube, the sample collection—which occurs at the lower end of the tube by passage of analyte into the flow-through cell—can be positioned or located at the desired point within the system to be examined. The probe can thus be designed to be both compact as well as long. The differences herein would essentially only be in the length of the incoming and outgoing channels and the length of the probe body.

A unit comprised of membrane and membrane holder can, for example, be screwed onto the probe. However, other coupling possibilities are possible.

BRIEF DESCRIPTION OF THE DRAWINGS

In the following the invention will be described in greater detail on the basis of the illustrative embodiment shown in the figures, which is intended to serve only for explaining the invention without limiting the scope of the invention in any way. In the drawings there is shown

DETAILED DESCRIPTION OF THE INVENTION

Figure 1:
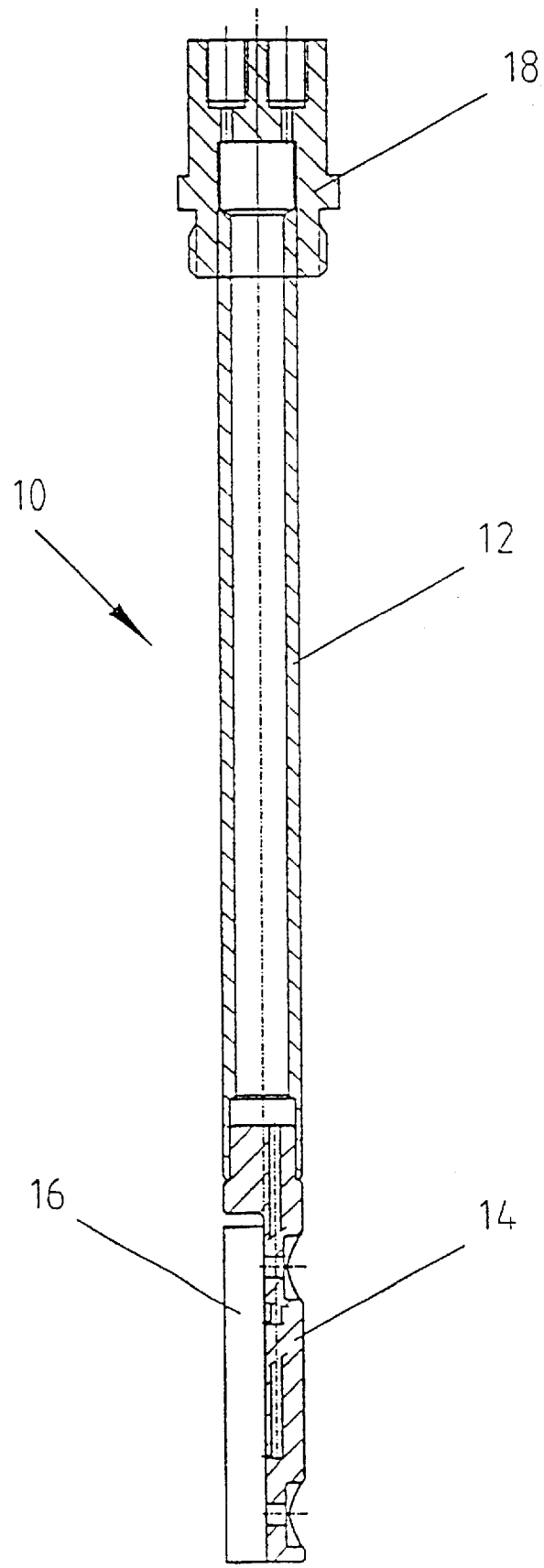
FIG. 1: an illustrative embodiment of the inventive probe as a whole.

FIG. 1 shows the probe indicated overall with reference number 10 in a longitudinal section perpendicular to the plane in which the membrane extends. The illustrative embodiment of the probe 10 is comprised of a submersion tube 12, a probe part 14 having a recess for receiving the unit comprised of a membrane and a membrane holder, which probe part is shown in greater detail in FIG. 4, the schematically represented unit 16 comprised of membrane and membrane holder, which is shown in greater detail in FIG. 2, as well as connection cap 18 shown in FIG. 5. The details of this illustrative embodiment of the probe are described in greater detail below with reference to FIGS. 2 through 5.

Figure 2A:
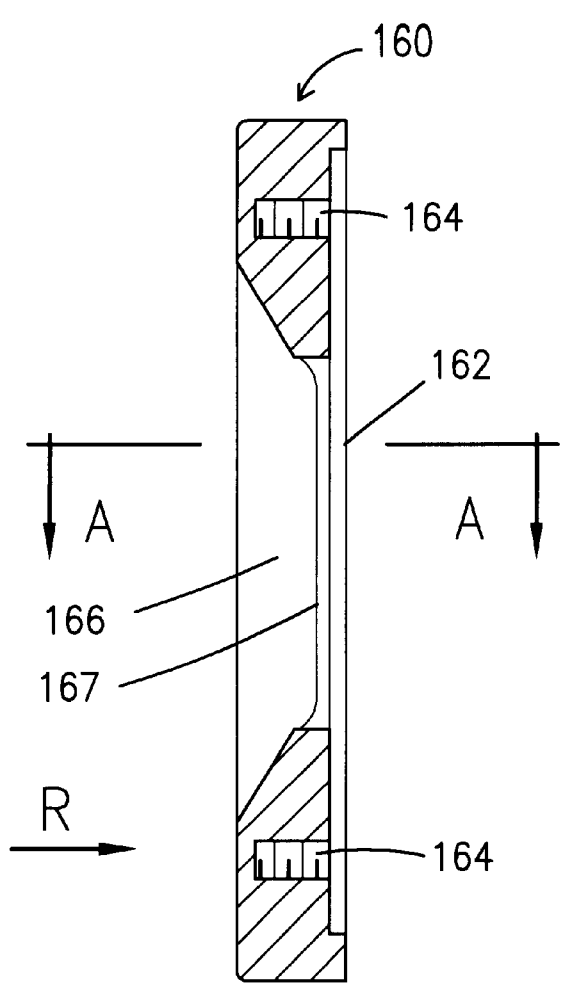
FIG. 2: a membrane holder for the probe of FIG. 1 shown for illustrative purposes in various views or sections a), b), c)
Figure 2B:
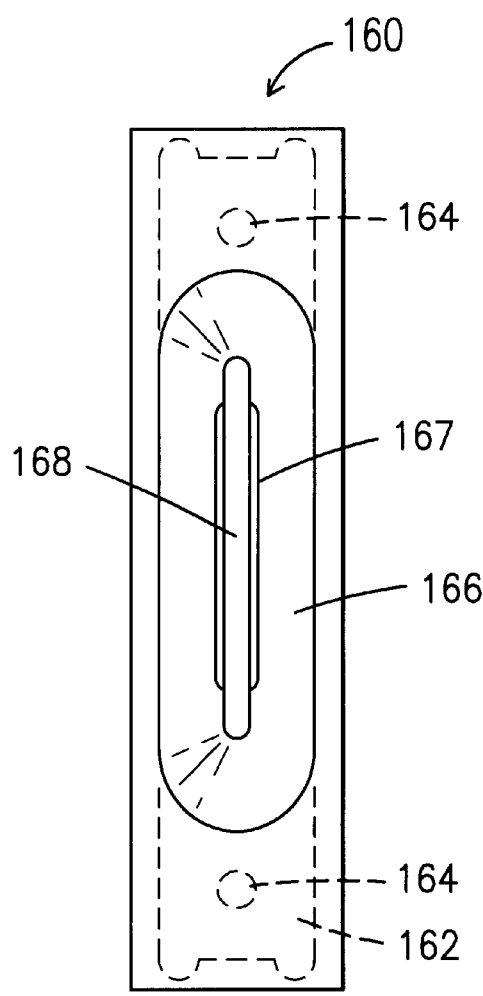
Figure 2C:
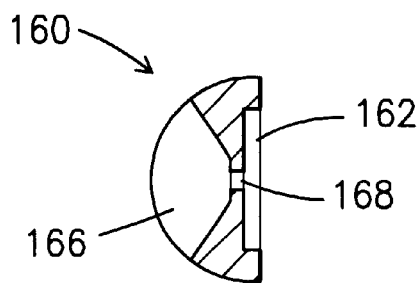

FIG. 2 shows the membrane holder 160 in a sectional view a) oriented perpendicular to a not shown membrane, a view b) in the direction of the arrow R shown in FIG. 2a) and a transverse sectional view c), seen in the direction of the arrows A—A from FIG. 2a). On the one side of the membrane holder 160, which in the assembled position lies flat against the probe part 14, a recess 162 is formed in, in which the membrane and in certain cases supplemental seals can be introduced. The through-holes 164 serve for securing the membrane holder 160 to the probe part 14 shown in FIGS. 1 and 4. On the opposite side of the membrane holder a recess 166 is milled or machined into the membrane holder 160, of which the floor area is here indicated with reference number 167. In the center of the recess 166 there is—in this embodiment corresponding approximately with the floor area 167—a through hole 168. A gland is formed in the membrane holder 160 by the recess 166 and the through hole 168, which exposes only a predetermined surface area of the membrane introduced in the recess 162.

Figure 3:
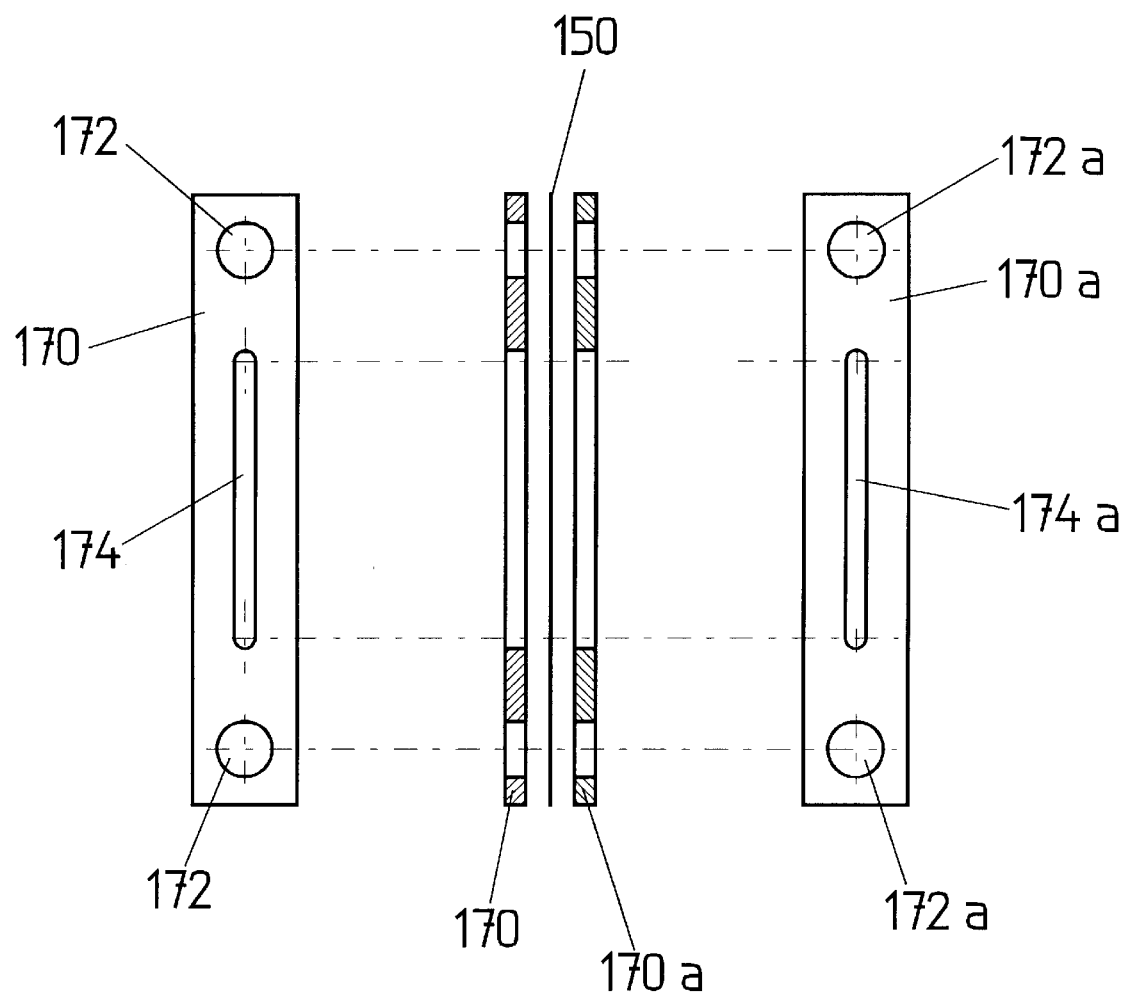
FIG. 3: a membrane seal with slit like openings for the same illustrative embodiment.

FIG. 3 shows a membrane seal 170, as it is introduced in the recess 162 of the membrane holder 160 for sealing the membrane against the probe part 14 on the one hand and the membrane holder 160 on the other hand. The membrane seals 170, 170a exhibit two circular through holes or passageways 172, 172a through which, in the assembled condition, the screws can extend to the probe part 14 for securing the unit 16, and an elongated through hole 174, which is covered over by the through hole 168 in the membrane holder. For sealing in the probe, a thin membrane, which could for example be comprised of a dialysis membrane, there is provided in the here illustrated embodiment, that the membrane 150 in the shape of a rectangle corresponding to the surface area of the recess 162 is introduced between two membrane seals 170, 170a shown in FIG. 3, and this sandwich structure is then introduced into the recess 162. The seals 170, 170a can be comprised for example of silicon. In the assembled position, the two membrane seals 170, 170a seal the membrane 150 on the one hand against the membrane holder 160, and on the other hand against the probe part 14. Therein the through-hole 174, 174a in the membrane seal 170 lying against the membrane holder, together with the through-hole 168 in the membrane holder 160, forms a gland which exposes only a predetermined surface area of the membrane to the medium being examined. On the other side, the through holes 174, 174a of the adjacent membrane seal 170, 170a laid against the probe part 14 together with the membrane and the probe body forms an elongate flow-through cell, which can be seen by reference to FIG. 4.

Figure 4A:
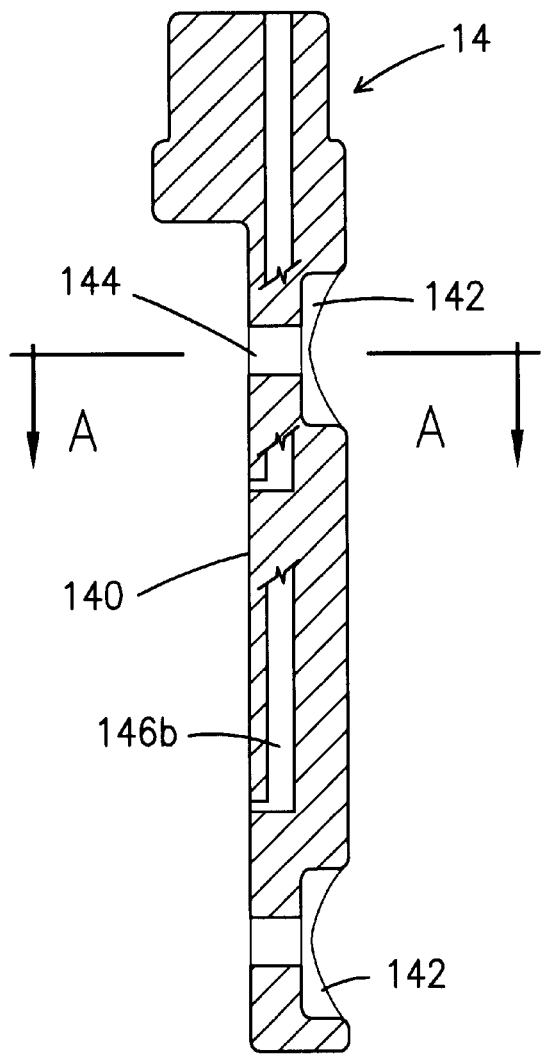
FIG. 4: the part of the probe for receiving the membrane of the embodiment shown in FIG. 1, without the membrane and the membrane holder, in various sections or views a), b), c)
Figure 4B:
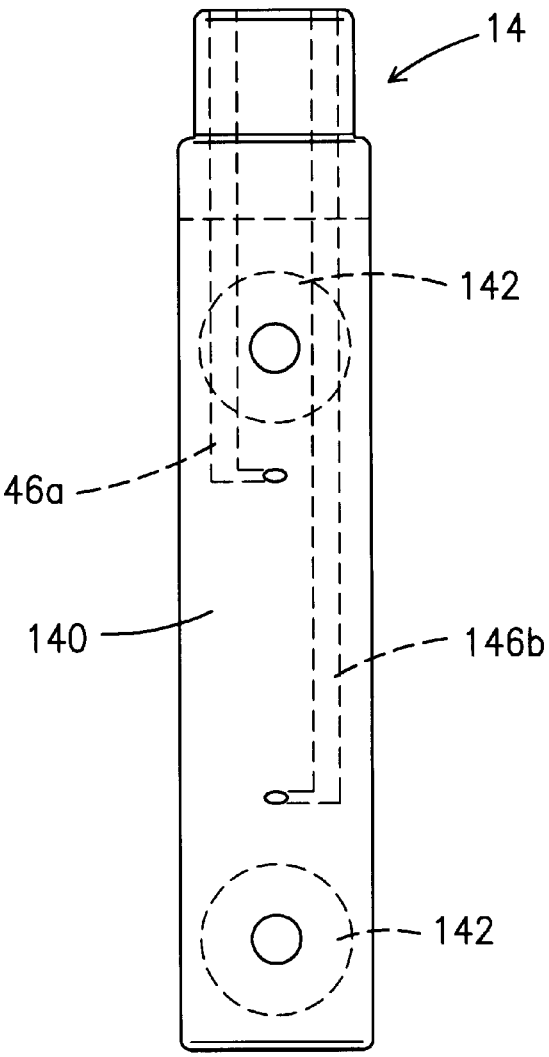
Figure 4C:
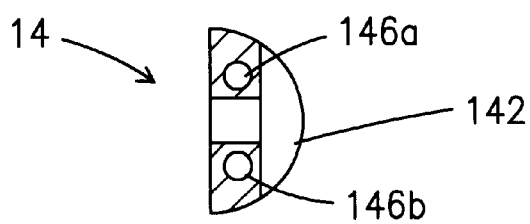

FIG. 4 shows the probe part 14 for receiving the unit 16, which unit is comprised of membrane and membrane holder, in a longitudinal section a) perpendicular to the plane of the membrane, a top view b) of the surface 140 of the probe part 14 lying opposite to the membrane and a sectional view c), seen along the arrow A—A in FIG. 4a).

FIG. 4a) shows two through-holes 142, through which two screws can be inserted, with which the membrane holder 160 shown in FIG. 2 together with the membrane and two of the membrane seals shown in FIG. 3 can be connected as a assembled unit 16 with the probe 10 or as the case may be probe part 14. The unit 16 is fittingly engaged thereby in the recess 144 formed in the probe part 14. The incoming and outgoing lines 146a) and 147b) lead, as can be seen particularly from FIG. 4b)—in this embodiment to the end-open surface 140 lying opposite to the membrane end, since the flow-through cell is embedded or formed in the membrane seal 170 shown in FIG. 3 and is bordered or limited by the membrane and the surface 140 by the seal passageway 174. The acceptor medium flows during measurement through the incoming line 146a or b into the probe, then through the flow-through cell lying in front of the illustration plane of FIG. 4, and then out of the probe through the outgoing line 146b or a.

Figure 5A:
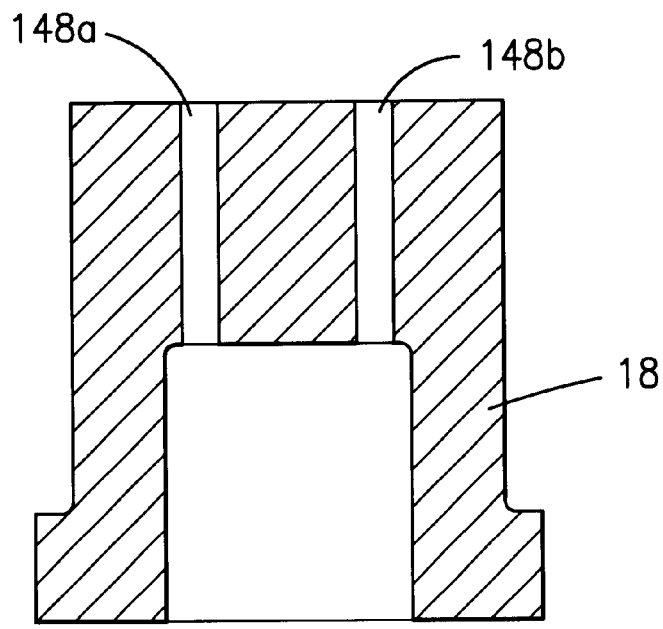
FIG. 5: a cap-shaped cover for the illustrative embodiment of the probe with connections for the incoming and outgoing lines, in various sectional views a) and b)
Figure 5B:
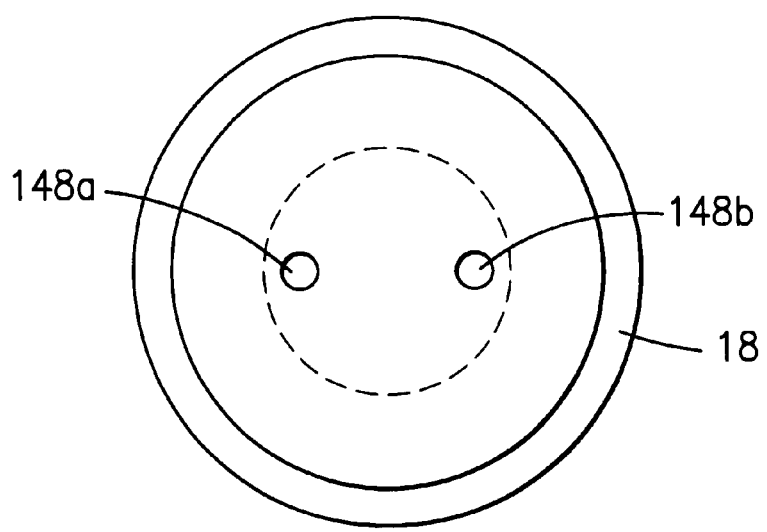

The connections for the incoming and outgoing lines 146a, 146b are shown in FIGS. 5a (cross sectional view) and 5b (top view) and are located in the probe cap 18 as fittings in the connection lines 148a and 148b for accepting and transferring the acceptor medium, for example to the measurement unit.

Figure 6:
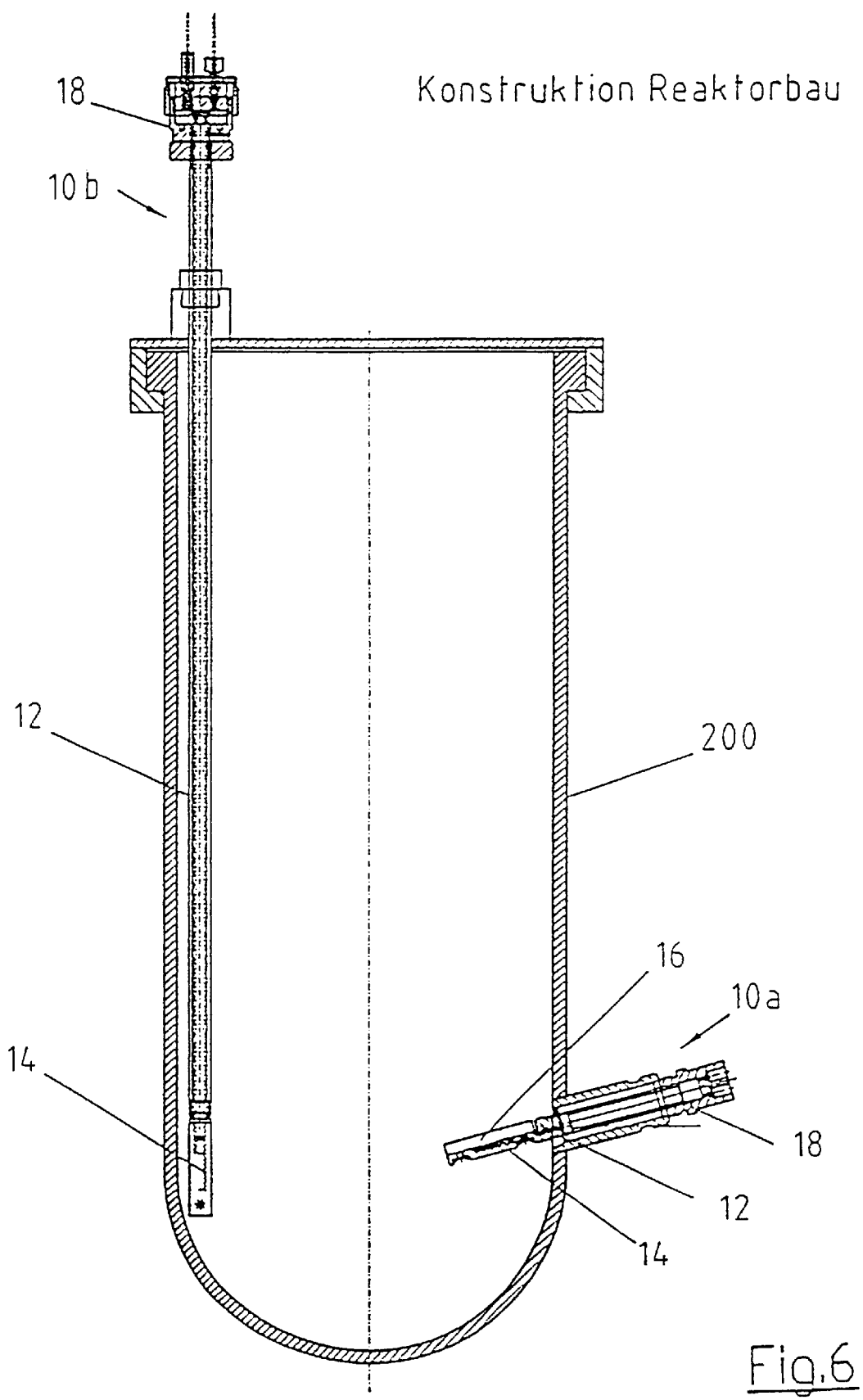
FIG. 6: an example for two different employment possibilities of the inventive probe in two different illustrative embodiments.

Finally, FIG. 6 shows two different embodiments of the inventive probe in assembled condition in a reactor 200, and more specifically first as a compact probe 10a and second as a probe 10b with a long submersion tube 12 (with the same construction components indicated using the same reference numbers). The probe can be adapted to the most various assembly situations and demands.

What is claimed is:

1. A probe (10) for collection of a sample of an analyte situated in a fluid medium, comprising
   a probe body (12) including a probe part (14),
   a membrane holder (160) located at the probe part (14),
   a membrane unit comprising an analyte permeable membrane, the membrane introduced between first and second membrane seals (170), said membrane unit being provided between said probe part (14) and said membrane holder (160), wherein the membrane unit via the membrane holder (160) is releasably and sealingly securable to the probe part (14), wherein said first and second membrane seals (170) have respectively one through-hole (174), wherein said first membrane seal through hole faces the membrane and the probe body part (14), and wherein said second membrane seal through hole faces the membrane and the membrane holder (160),
   a flow-through cell defined in said probe (10) and located behind the membrane,
   at least one incoming line and one outgoing line leading to and from the flow-through cell,
   wherein said membrane holder (160) and said membrane unit form an unit replaceably removable from the probe part (14), and
   wherein the membrane holder (160) forms a gland and in association with the through holes (174) of the membrane seals (170) exposes only a predetermined limited surface area of the membrane covering the flow-through cell.

2. A probe (10) according to claim 1, wherein said flow-through cell extends along the membrane in an elongate shape.

3. A probe (10) according to claim 2, wherein said flow-through cell is formed as a channel bordered by the membrane and optionally an associated membrane seal (170).

4. A probe (10) according to claim 2, wherein said incoming and outgoing lines are provided at the side of the elongate flow-through cell opposite the side exposed to the membrane.

5. A probe (10) according to claim 1, wherein said probe (10) is tube-shaped, wherein the flow-through cell, and an unit formed by the membrane and the membrane holder (160) are provided at one end of the tube-shaped probe, and wherein the incoming end outgoing line(s) lead to connections at the other end of the tube-shaped probe.

6. A probe (10) according to claim 1, wherein the membrane and the membrane holder (160) form a unit that is screwed into the probe (10).

7. A probe (10) for collection of a sample of an analyte situated in a fluid medium, comprising
- a probe body (12) including a probe part (14),
- a membrane holder (160) located at the probe part (14),
- a membrane unit comprising an analyte permeable membrane, the membrane introduced between first and second membrane seals (170), said membrane unit being provided between said probe part (14) and said membrane holder (160), wherein the membrane unit via the membrane holder (160) is releasably and sealingly securable to the probe part (14), wherein said first and second membrane seals (170) have respectively one through-hole (174), wherein said first membrane seal through hole faces the membrane and the probe body part (14), and wherein said second membrane seal through hole faces the membrane and the membrane holder (160),
- a flow-through cell defined in said probe (10) located behind the membrane,
- at least one incoming line and one separate outgoing line leading to and from the flow-through cell, for conveying an acceptor medium through the flow-through cell for accepting said analyte passing through said membrane,
- wherein said membrane holder (160) and said membrane unit form an unit replaceably removable from the probe part (14), and
- wherein the membrane holder (160) forms a gland and in association with the through holes (174) of the membrane seals (170) exposes only a predetermined limited surface area of the membrane covering the flow-through cell.

* * * * *